US007126018B2

(12) United States Patent
Poppe

(10) Patent No.: US 7,126,018 B2
(45) Date of Patent: Oct. 24, 2006

(54) METHODS FOR THE PREPARATION OF POLYOL ESTERS THAT ARE LIGHT IN COLOR

(75) Inventor: George B. Poppe, Forsyth, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 191 days.

(21) Appl. No.: 10/758,267

(22) Filed: Jan. 16, 2004

(65) Prior Publication Data

US 2005/0159610 A1    Jul. 21, 2005

(51) Int. Cl.
*C11C 3/00*     (2006.01)
(52) U.S. Cl. ............... 554/168; 554/167; 554/163
(58) Field of Classification Search ........... 554/163, 554/167, 168
See application file for complete search history.

(56) References Cited

U.S. PATENT DOCUMENTS

| 3,669,848 | A | 6/1972 | Seiden |
| 6,965,043 | B1 * | 11/2005 | Kenneally et al. .......... 554/167 |

FOREIGN PATENT DOCUMENTS

DE     101 21 866     * 11/2002

OTHER PUBLICATIONS

Chem. Abstr. of DE-10121866, Nov. 7, 2002.*
"Color: Lovibond Method Using Color Glasses Calibrated in Accordance with the Lovibond Tintometer Color Scale, Sampling and Analysis of Commercial Fats and Oils, American Oil Chemists' Society Official Method Cc 13e-92, Revised 2002," in *Official Methods and Recommended Practices of the AOCS*, 5th ed., Firestone, D., et al., eds., American Oil Chemists' Society, Champaign, IL, pp. 1-2 (1998).
Celades, R., and Paquot, C., "Preparation des Esters de Polyoxyéthylèneglycols par Glycolyse," in *Chemistry, Physics and Application of Surface Active Substances*, Proceedings of the IVth Int'l Congress on Surface Active Substances, vol. I., Asinger, F., ed., Gordon and Breach Science Publishers, New York, NY, pp. 249-255 (1967).
Gupta, M., "Manufacturing Processes for Emulsifiers" in *Bailey's Industrial Oil and Fat Products*, Ch. 11, vol. 4, 5th ed., Hui, Y.H., ed., John Wiley & Sons, Inc., New York, NY, pp. 569-601 (1996).
Jiratumnukul, N., and Van De Mark, M.R., "Preparation of Glycol Esters of Soybean Oil Fatty Acids and Their Potenial as Coalescent Aids in Paint Formulations," *JAOCS* 77:691-697, AOCS Press (2000).
Sonntag, N.O.V., "Fat Splitting, Esterification, and Interesterification" in *Bailey's Industrial Oil and Fat Products*, vol. 2, 4th ed., Swern, D., ed., John Wiley & Sons, Inc., New York, NY, pp. 97-173 (1982).

* cited by examiner

*Primary Examiner*—Deborah D. Carr
(74) *Attorney, Agent, or Firm*—Sterne, Kessler, Goldstein & Fox, P.L.L.C.

(57) ABSTRACT

The present invention is directed to a process of producing polyol esters possessing desirable composition and color. Preferably, such a process does not require molecular distillations or decoloration steps to yield a light-colored polyol ester composition. Materials that are dark in color are often produced during the esterification of polyols with vegetable oil fatty acids. It has been discovered that the present process yields the desired ester products that are light in color. The present process comprises an esterification of a polyol, such as propylene glycol, and a fatty acid ester, such as a vegetable oil fatty acid methyl ester, in the presence of a catalyst and borohydride, wherein a polyol ester having a Lovibond color below about 0.6 Red and below about 1.5 Yellow is produced.

57 Claims, No Drawings

METHODS FOR THE PREPARATION OF POLYOL ESTERS THAT ARE LIGHT IN COLOR

BACKGROUND OF THE INVENTION

1. Field of the Invention

This invention relates to a novel process for producing a polyol ester composition which possesses a desirable composition and color.

2. Related Art

During the past few decades, water-borne coatings have found broad acceptance in architectural as well as industrial applications and are expected to have continued good growth rates in the coating industry. The driving forces behind this trend are based upon both environmental and economic concerns to reduce volatile organic compounds (VOC) of most coating materials. Traditionally, latex coatings, based upon small particles (emulsions) of a synthetic resin such as acrylic polymers, have required the use of a coalescing aid in substantial quantities. The coalescing aid in latex coatings is added to improve the filming properties of the coatings. The function of the coalescing aid is to soften the latex particles so they can flow together and form a continuous film with optimal film properties after the water has evaporated. Without the coalescing aid, the latex coatings may crack and not adhere to the substrate surface when dry at ambient temperatures.

Alcohol esters and ether alcohols, such as ethylene glycol monobutyl ether and TMB (2,2,4-trimethyl-1,3-pentanediol monoisobutyrate), are widely used as coalescing aids in the latex coatings industry. These chemicals are volatile and are counted as VOC in the paint.

Although newer formulations of water-borne paints and coatings have reduced the amount of coalescing aids, they have not eliminated them. It is estimated that the market for latex paint coalescing aids is on the order of 120 million pounds in the U.S. and perhaps twice that amount globally. Currently, nearly all of this material is lost into the atmosphere each year. Proposed regulations have limited the level of VOC in latex paints even further.

Recently, glycol esters of unsaturated fatty acids (such as the propylene glycol monoesters (PGME) of vegetable oil fatty acids) have been shown to perform in the same way as TMB to cause the latex particles to coalesce and form a cohesive film (N. Jiratumnukul & M. Van De Mark, JAOCS, vol. 77, no. 7, 691, 2000). Due to the large relative size (molecular weight) of these unsaturated esters, these coalescing aids are essentially, non-volatile, and therefore do not contribute to the VOC of the coating. Instead of evaporating into the air over a few days as in the case of conventional coalescing aids, these glycol esters oxidize and remain within the film. Over the course of a few days the coating dries and becomes harder and more durable without releasing VOC into the atmosphere. It is important that the fatty acids be primarily polyunsaturated fatty acids to facilitate this oxidative reaction. The primary coalescing aid is propylene glycol monoesters (PGME) of polyunsaturated fatty acids.

The effect of PGME coalescent on yellowing in the paint film is one concern. Another issue is the visual color of the liquid PGME product to be used. To compete in the paint industry with TMB (a color-less water-clear liquid), a clear, almost colorless liquid PGME is needed. Color can be measured using a Lovibond tintometer, which is an instrument for evaluating oil colors on the Lovibond scale (a standard scale in the industry). The color of a monoester mixture can be determined by comparing the monoester mixture product to standard reference samples.

In general, the preparation of fatty acid esters of polyols (such as propylene glycol) is possible from a number of routes. For example, propylene glycol and triglycerides can be reacted together using an alkaline catalyst to give a reaction product comprising monoesters of propylene glycol, propylene glycol diesters, monoglycerides, diglycerides, and triglycerides, after removal of the excess propylene glycol and glycerol (Hui, Y. H., "Manufacturing Processes for Emulsifiers" in Bailey's Industrial Oils and Fat Products, John Wiley & Sons, Inc.(1996) $5^{th}$ Ed., Vol. 4, pp. 569–601).

A second route is through the reaction of propylene glycol with fatty acids or fatty acid esters, such as methyl or ethyl esters of fatty acids (Swern, D., "Fat Splitting, Esterification, and Interesterification" in Bailey's Industrial Oils and Fat Products, John Wiley & Sons, Inc.(1982) $4^{th}$ Ed., Vol. 2, pp. 97–173). An acid such as para-toluene sulfonic acid catalyzes the esterification of palmitic acid and propylene glycol (U.S. Pat. No. 3,669,848). Reaction of fatty acid methyl esters with glycols was accomplished with the addition of metallic sodium as catalyst and the evolution of methanol (R. Celades and C. Paquot, Chem. Phys. Appl. Surface Active Subst., Proc. $4^{th}$ Int. Congr. (1964; published 1967) 1, 249–255). The product from these reactions will generally be a mixture comprising primarily mono- and diesters of propylene glycol after the removal of water or the low-boiling alcohol (ethanol, methanol, etc.), byproducts and any excess starting reactants.

A third route is combining propylene oxide with fatty acid, leading to a mixture of monoester isomers.

A fourth route is combining propylene glycol with an acid chloride of a fatty acid.

The final product composition of these processes can be described in terms of the ratio of mono- to diesters comprising the product. The composition of the end product can be controlled by varying the amounts of glycol with respect to fatty acid reagent (methyl ester, fatty acid or oil), and through manipulating the reaction conditions. The above reaction processes, however, consistently generate color during the preparation of the propylene glycol fatty acid ester product.

If a very high propylene glycol monoester product was desired, in general, a distillation process was the most widely used technique for such purification. Due to the high molecular weight of the propylene glycol fatty acid esters, an expensive subsequent molecular distillation was required to obtain higher monoester concentration. The crude monoester mixture is distilled under high vacuum, in a short path distillation process. The distillate generally comprises greater than 90% (by weight) monoesters. The remaining material generally comprises mainly propylene glycol diesters, monoglycerides and/or diglycerides, depending upon the starting reactants used. Previously, this molecular distillation was the only method which yielded a nearly colorless propylene glycol monoester product of unsaturated fatty acids.

As described above, it is desirable to prepare a propylene glycol fatty acid monoester mixture of acceptable color for use as a non-volatile coalescing aid for latex paints. A dark-colored monoester mixture is not suitable for incorporation into coating compositions. It would be useful to develop a process for producing propylene glycol monoesters of polyunsaturated fatty acids in which the product of said process contains a high amount (at least about 85%) of monoester and has the desirable characteristic of a light color, without the need for purification through a molecular distillation process or a decoloration step.

BRIEF SUMMARY OF THE INVENTION

The present invention is directed to a process of producing polyol esters possessing desirable composition and color. Preferably, such a process does not require molecular distillations or decoloration steps to yield a light-colored polyol ester composition. Materials that are dark in color are often produced during the esterification of polyols with vegetable oil fatty acids. It has been discovered that the present process yields the desired ester products that are light in color. The present process comprises an esterification of a polyol, such as propylene glycol, and a fatty acid ester, such as a vegetable oil fatty acid methyl ester, in the presence of a catalyst and borohydride, wherein a polyol ester having a Lovibond color below about 0.6 Red and below about 1.5 Yellow is produced.

DETAILED DESCRIPTION OF THE INVENTION

In general, the present invention describes a process of preparing a polyol ester composition which comprises, a transesterification reaction in the presence of a fatty acid $C_{1-5}$ alkyl ester, a polyol, a catalyst and a sufficient amount of borohydride to inhibit color formation during the reaction.

General methods known in the art for transesterification or esterification can be modified to use a borohydride to produce a lighter color ester product. For example, sodium borohydride may be amenable in transesterification or esterification reactions that are alkaline in nature.

In a preferred embodiment, the present invention describes a process for producing a monoester mixture comprising, combining a fatty acid $C_{1-5}$ alkyl ester with a polyol in the presence of a catalyst and a borohydride, and heating, wherein a polyol monoester mixture that is light in color is produced.

In a preferred embodiment of this aspect, the above process does not require a molecular distillation or decoloration step on the polyol ester composition to produce a polyol composition is high in monoester content and light in color. Decoloration steps avoided by this process include carbon treatment, bleaching and similar processes that are known in the art to remove undesirable color.

In this aspect of the present invention, the combined fatty acid $C_{1-5}$ alkyl ester and polyol is heated in the presence of catalyst and borohydride to effect transesterification, wherein development of color is inhibited. Preferably, the combined starting materials are heated to a temperature between about 70° C. and about 160° C. under a vacuum in an inert atmosphere, such as $N_2$, Ar or $CO_2$. More preferably, the temperature range is from about 100° to about 140° C. Preferably, the vacuum is sufficient to remove the $C_{1-5}$ alcohol by-product. Determination of a sufficient amount of vacuum is well within the purview of a skilled artisan. The vacuum will also aid in removing $O_2$ from the headspace and combined starting materials. It is preferred that the atmosphere is free of $O_2$ and is composed of an inert gas such as those listed above. The combined fatty acid $C_{1-5}$ alkyl ester and polyol in the presence of a catalyst and borohydride is heated slowly to the above temperature range. During the process of transesterification, the temperature is maintained in the above range until sufficient conversion to product has occurred. The reaction mixture is then cooled and the catalyst is neutralized with acid, such as citric acid or phosphoric acid.

A polyol ester is a composition that contains monoesters and diesters, as well as other impurities. In a preferred embodiment, the present method yields a monoester mixture.

A monoester mixture is a composition comprising a high percentage of monoester in terms of the ratio of mono- to diesters comprising the product. A monoester mixture can contain some residual diesters, fatty acid $C_{1-5}$ alkyl esters, monoglycerides and other impurities depending on the starting materials. Preferably, the product is a monoester mixture containing at least about 80 percent monoesters. More preferably, the present process yields a monoester mixture that comprises at least about 85 percent monoesters. When the starting polyol is propylene glycol, the process yields a propylene glycol monoester (PGME) mixture. In a most preferred embodiment, the present process can be used to produce a PGME that contains at least about 80 percent monoesters.

Fatty acid esters include fatty acid alkyl esters, wherein the alkyl group is a $C_{1-5}$ alkyl. More preferred esters include fatty acid $C_{1-5}$ alkyl esters derived from a polyunsaturated vegetable oil. In preferred embodiments, the fatty acid $C_{1-5}$ alkyl ester contains less than about 2 percent of C18:3 or higher polyunsaturated fatty acids. More preferably, the fatty acid $C_{1-5}$ alkyl ester contains less than about 1 percent of C18:3 or higher polyunsaturated fatty acids. Also preferred are fatty acid $C_{1-5}$ alkyl esters containing less than about 2 percent linolenic acid. More preferably the linolenic content is less than about 1 percent. Preferred fatty acid $C_{1-5}$ alkyl esters having the above properties also have $C_{1-5}$ alkyl moieties selected from the group consisting of methyl, ethyl, propyl and n-propyl. In the most preferred embodiment, the ester is a fatty acid methyl ester.

In the case of the preferred fatty acid methyl ester, low moisture refined sunflower oil was added to a large molar excess of anhydrous methanol. The mixture was combined with an alkaline catalyst and heated at methanol reflux for about 2 hours. Upon cooling of the mixture and neutralizing of the catalyst, the fatty acid methyl ester layer is collected and washed with water to remove any salts and water-soluble impurities. Any residual moisture or methanol can be stripped from the methyl esters by techniques well known in the art.

The vegetable oils suitable for preparing the fatty acid $C_{1-5}$ alkyl ester can include genetically modified oil, soybean oil, linseed oil, corn oil, sunflower oil, canola oil, rapeseed oil, coconut oil, palm kernel oil, palm oil, cottonseed oil, peanut oil, olive oil, tall oil, safflower oil and derivatives and mixtures thereof. Preferably, the vegetable oil is a polyunsaturated oil selected from the group above. Most preferably, the polyunsaturated vegetable oil is low in C18:3 or higher fatty acids. Although any polyunsaturated oil that has sufficiently low levels of C18:3 or higher fatty acids is suitable for the present method, preferably, the vegetable oil is safflower oil, sunflower oil or corn oil. Preferred oils contain less than about 2 percent of C18:3 or higher polyunsaturated fatty acids. More preferably, the oils contain less than about 1 percent of C18:3 or higher polyunsaturated fatty acids. Also preferred are polyunsaturated vegetable oils containing less than about 2 percent linolenic acid. More preferably, the linolenic content is less than about 1 percent.

The fatty acid $C_{1-5}$ alkyl ester starting material can be prepared by methods well known in the art, such as a transesterification reaction between a $C_{1-5}$ alcohol and the vegetable oil. In preferred embodiments, the alcohol is a $C_{1-5}$ alcohol, wherein the transesterifcation of said alcohol yields a fatty acid $C_{1-5}$ alkyl ester. Preferred alcohols are selected from the group consisting of methanol, ethanol, isopropanol and n-propanol. Most preferably, the alcohol is methanol, wherein the transesterification yields a fatty acid methyl ester.

Preferably, the fatty acid $C_{1-5}$ alkyl ester is distilled prior to using in the present method. Such a distillation is distinguishable from a molecular distillation of the polyol ester product wherein the final ester mixture is purified, i.e. enriched in a certain ester component. The fatty acid $C_{1-5}$ alkyl ester distillation step produces a generally water-clear distillate. The distillation proceeds under reduced pressure and elevated temperatures such that a distilled fatty acid $C_{1-5}$ alkyl ester is collected as the distillate. Such distillation techniques are well known in the art. An advantage of performing a distillation is that the process is straightforward and inexpensive. Unlike molecular distillation, it does not require complex equipment or exceedingly high vacuum. The water-clear fatty acid $C_{1-5}$ alkyl ester distillate is the preferred starting material for the present process of producing a polyol ester, such as PGME, that is high in monoester content and light in color. In preferred embodiments, the distillate is a fatty acid $C_{1-5}$ alkyl ester wherein the $C_{1-5}$ alkyl is a methyl, ethyl, isopropyl or n-propyl group. Most preferably, the distillate is a fatty acid methyl ester. Generally, the fatty acid $C_{1-5}$ alkyl ester distillate has a peroxide value below about 50. More preferably, the peroxide value is below about 25. Most preferably, the fatty acid $C_{1-5}$ alkyl ester distillate has a peroxide value below about 10.

The polyol is selected from dihydroxy polyols, which include ethylene glycol, propylene glycol, diethylene glycol, dipropylene glycol and the like. The preferred polyol is propylene glycol, which includes individual isomers and d,l-propylene glycol.

As outlined above, it is preferable that the fatty acid $C_{1-5}$ alkyl ester is distilled prior to combining with a polyol. Thus, the present method further comprises, distilling said fatty acid $C_{1-5}$ alkyl ester to prepare a distilled fatty acid $C_{1-5}$ alkyl ester prior to combining with the polyol in the presence of a catalyst and borohydride. Preferably, the distilled starting material is a fatty acid methyl ester derived from a vegetable oil as disclosed herein.

The catalyst selected for use in the present method can be any catalyst generally known in the art for use in transesterification or esterification reactions. Preferably, the catalyst used in the present process is an alkaline catalyst. More preferably, the catalyst is selected from the group consisting of sodium methoxide, sodium ethoxide, potassium methoxide and potassium ethoxide. Most preferably, the catalyst used in the present process is sodium methoxide.

The present process produces a polyol ester composition that is light in color, wherein the present process utilizes borohydride and produces a polyol ester that is lighter in color than a polyol ester composition prepared by the same reaction without sodium borohydride. The present process preferably yields polyol ester compositions possessing a color that is below about 0.6 Red and below about 1.5 Yellow on the Lovibond scale (American Oil Chemists' Society Official Method cC 13e–92 in *Sampling and Analysis of Commercial Fats and Oils*, pp. 1–3). More preferably the color is below about 0.4 Red and below about 1.0 Yellow.

The present invention is directed to the use of borohydride to inhibit the formation of color during the ester formation between a polyol and a fatty acid $C_{1-5}$ alkyl ester. Preferably, the borohydride material is selected from the group consisting of sodium borohydride, potassium borohydride and lithium borohydride. It has been discovered that sodium borohydride present in an amount to inhibit color formation yields an ester product that is lighter than an ester product produced by the same method in the absence of sodium borohydride. By routine experimentation, a skilled artisan will quickly be able to determine the amount of borohydride necessary for a given reaction. Preferably, the borohydride is present in an amount between about 1.0 percent and about 0.0001 percent by weight of the reactants and catalyst. More preferably, the amount of borohydride is between about 0.1 percent to about 0.001 percent. It has been found that sodium borohydride present in an amount between about 0.1 percent to about 0.001 percent by weight of the reactants and catalyst yields a glycol monoester mixture that possesses the desirable light color.

The polyol ester composition produced by the present method preferably has a peroxide value below about 50. More preferably, the peroxide value is below about 25. Most preferably, the peroxide value is below about 10.

In another aspect, the present invention is directed to a method of producing a monoester mixture comprising, (a) distilling a fatty acid $C_{1-5}$ alkyl ester containing less than about 2 percent C18:3 or higher polyunsaturated fatty acids to produce a distilled fatty acid $C_{1-5}$ alkyl ester, (b) combining said distilled fatty acid $C_{1-5}$ alkyl ester with a polyol to produce a first mixture, (c) introducing a catalyst and borohydride to said first mixture, (d) heating said first mixture to a temperature between about 70° C. and about 160° C. to produce a second mixture, (e) cooling and neutralizing said second mixture with an acid, and (f) separating a monoester mixture from said second mixture, wherein a monoester mixture is produced.

In a preferred embodiment of this aspect, the above process does not require a molecular distillation or decoloration step on the monoester mixture to produce a monoester mixture that is high in monoester content and light in color.

In this aspect of the present invention, the combined fatty acid $C_{1-5}$ alkyl ester and polyol is heated in the presence of catalyst and borohydride to effect a transesterification, wherein development of color is inhibited. Preferably, the combined starting materials are heated to a temperature between about 70° C. and about 160° C. under a vacuum in an inert atmosphere, such as $N_2$, Ar or $CO_2$. More preferably, the temperature range is from about 100° to about 140° C. Preferably, the vacuum is sufficient to remove the $C_{1-5}$ alcohol by-product. A skilled artisan can easily determine a sufficient amount of vacuum necessary. The vacuum will also aid in removing $O_2$ from the headspace and combined starting materials. It is preferred that the atmosphere is free of $O_2$ and is composed of an inert gas such as those listed above. The combined fatty acid $C_{1-5}$ alkyl ester and polyol in the presence of a catalyst and borohydride is heated slowly to the above temperature range. During the process of transesterification, the temperature is maintained in the above range until sufficient conversion to product has occurred. The reaction mixture is then cooled and the catalyst is neutralized with acid, such as citric acid or phosphoric acid. The monoester mixture can then be separated from residual unreacted polyol by means that are well known in the art.

In this embodiment, the present process produces a monoester mixture. A monoester mixture is a composition comprising a high percentage of monoester in terms of the ratio of mono- to diesters comprising the product. A monoester mixture can contain some residual diesters, fatty acid $C_{1-5}$ alkyl esters, monoglycerides and other impurities depending on the starting materials. Preferably, the product is a monoester mixture containing at least about 80 percent monoesters. More preferably, this embodiment yields a monoester mixture that comprises at least about 85 percent monoesters. When the starting polyol is propylene glycol, the process yields a propylene glycol monoester (PGME) mixture. In a most preferred embodiment, the present process can be used to produce a PGME that contains at least about 80 percent monoesters.

The present embodiment comprises distilling a fatty acid $C_{1-5}$ alkyl ester starting material. The distillation process is described above. Preferably, the fatty acid $C_{1-5}$ alkyl ester is derived from a vegetable oil. More preferred esters include fatty acid $C_{1-5}$ alkyl esters derived from a polyunsaturated vegetable oil. In preferred embodiments, the fatty acid $C_{1-5}$ alkyl ester contains less than about 2 percent of C18:3 or higher polyunsaturated fatty acids. More preferably, the fatty acid $C_{1-5}$ alkyl ester contains less than about 1 percent of C18:3 or higher polyunsaturated fatty acids. Also preferred are fatty acid $C_{1-5}$ alkyl esters containing less than about 2 percent linolenic acid. More preferably the linolenic content is less than about 1 percent. Preferred fatty acid $C_{1-5}$ alkyl esters having the above properties also have $C_{1-5}$ alkyl moieties selected from the group consisting of methyl, ethyl, propyl and n-propyl. In the most preferred embodiment, the ester is a fatty acid methyl ester.

The polyunsaturated vegetable oils suitable for preparing the fatty acid $C_{1-5}$ alkyl ester include genetically modified oil, soybean oil, linseed oil, corn oil, sunflower oil, canola oil, rapeseed oil, coconut oil, palm kernel oil, palm oil, cottonseed oil, peanut oil, olive oil, tall oil, safflower oil and derivatives and mixtures thereof. Preferably, the vegetable oil is a polyunsaturated vegetable oil selected from the group above. Most preferably, the polyunsaturated vegetable oil is low in C18:3 or higher fatty acids. Although any oil that has sufficiently low levels of C18:3 or higher fatty acids is suitable for the present method, preferably, the vegetable oil is safflower oil, sunflower oil or corn oil. Preferred oils contain less than about 2 percent of C18:3 or higher polyunsaturated fatty acids. More preferably, the oils contain less than about 1 percent of C18:3 or higher polyunsaturated fatty acids. Also preferred are polyunsaturated vegetable oils containing less than about 2 percent linolenic acid. More preferably, the linolenic content is below about 1 percent.

The monoester mixture produced by this embodiment preferably has a peroxide value below about 50. More preferably, the peroxide value is below about 25. Most preferably, the peroxide value is below about 10.

The polyol is selected from dihydroxy polyols, which include ethylene glycol, propylene glycol, diethylene glycol, dipropylene glycol and the like. The preferred polyol is propylene glycol, which includes individual isomers and d,l-propylene glycol.

The catalyst selected for use in this embodiment can be any catalyst generally known in the art for use in transesterification and esterification reactions. Preferably, the catalyst used in the present process is an alkaline catalyst. More preferably, the catalyst is selected from the group consisting of sodium methoxide, sodium ethoxide, potassium methoxide and potassium ethoxide. Most preferably, the catalyst used in the present process is sodium methoxide.

The present process utilizes a borohydride and produces a monoester mixture that is lighter in color than a monoester mixture prepared by the same reaction without a borohydride. The present method produces monoester mixtures that have a Lovibond color below about 0.6 Red and below about 1.5 Yellow. More preferably the color is below about 0.4 Red and below about 1.0 Yellow.

Regarding the amount of borohydride that is sufficient to perform this embodiment, by routine experimentation, a skilled artisan will quickly be able to determine the amount of borohydride necessary for a given reaction. Preferably, the borohydride material is selected from the group consisting of sodium borohydride, potassium borohydride, and lithium borohydride. Preferably, the borohydride is present in an amount between about 1.0 percent and about 0.0001 percent by weight of the reactants and catalyst. More preferably, the amount of borohydride is between about 0.1 percent to about 0.001 percent. It has been found that sodium borohydride present in an amount between about 0.1 percent to about 0.001 percent by weight of the reactants and catalyst yields a glycol monoester mixture that possesses the desirable light color.

The monoester mixture produced by this embodiment preferably has a peroxide value below about 50. More preferably, the peroxide value is below about 25. Most preferably, the peroxide value is below about 10.

In another aspect, the present invention is directed to a process of producing a monoester mixture comprising, combining a distilled fatty acid $C_{1-5}$ ester of a vegetable oil with a glycol in the presence of a catalyst and borohydride to produce a monoester mixture having a Lovibond color below about 0.6 Red and below about 1.5 Yellow. More preferably the color is below about 0.4 Red and below about 1.0 Yellow.

In a preferred embodiment of this aspect, a molecular distillation is not performed on the monoester mixture to produce the final monoester mixture having a having a Lovibond color below about 0.6 Red and below about 1.5 Yellow. More preferably the color is below about 0.4 Red and below about 1.0 Yellow.

In this aspect of the present invention, the combined distilled fatty acid $C_{1-5}$ alkyl ester and polyol is heated in the presence of catalyst and borohydride to effect transesterification, wherein development of color is inhibited. Preferably, the combined starting materials are heated to a temperature between about 70° C. and about 160° C. under a vacuum in an inert atmosphere, such as $N_2$, Ar or $CO_2$. More preferably, the temperature range is from about 100° to about 140° C. Preferably, the vacuum is sufficient to remove the $C_{1-5}$ alcohol by-product. A skilled artisan can easily determine a sufficient amount of vacuum necessary. Further, the vacuum will aid in removing $O_2$ from the headspace and combined starting materials. It is preferred that the atmosphere is free of $O_2$ and is composed of an inert gas such as those listed above. The combined fatty acid $C_{1-5}$ alkyl ester and polyol in the presence of a catalyst and borohydride is heated slowly to the above temperature range. During the process of transesterification, the temperature is maintained in the above range until sufficient conversion to product has occurred. The reaction mixture is then cooled and the catalyst is neutralized with acid, such as citric acid or phosphoric acid. The monoester mixture can then be separated from residual unreacted polyol by means that are well known in the art.

In this embodiment, the present process produces a monoester mixture. A monoester mixture is a composition comprising a high percentage of monoester in terms of the ratio of mono- to diesters comprising the product. The monoester mixture can contain some residual diesters and other impurities. Preferably, the product is a monoester mixture containing at least about 80 percent monoesters. More preferably, this embodiment yields a monoester mixture that comprises at least about 85 percent monoesters. When the starting polyol is propylene glycol, the process yields a propylene glycol monoester (PGME) mixture. In a most preferred embodiment, the present process can be used to produce a PGME that contains at least about 80 percent monoesters.

Preferably, the fatty acid $C_{1-5}$ ester is derived from a vegetable oil as outlined above. A distillation process for preparing a distilled fatty acid $C_{1-5}$ alkyl ester is also described above. More preferred esters include fatty acid $C_{1-5}$ alkyl esters derived from a polyunsaturated vegetable oil. In preferred embodiments, the fatty acid $C_{1-5}$ alkyl ester contains less than about 2 percent of C18:3 or higher polyunsaturated fatty acids. More preferably, the fatty acid $C_{1-5}$ alkyl ester contains less than about 1 percent of C18:3 or higher polyunsaturated fatty acids. Also preferred are fatty acid $C_{1-5}$ alkyl esters containing less than about 2 percent linolenic acid. More preferably the linolenic content is less than about 1 percent. Preferred fatty acid $C_{1-5}$ alkyl esters having the above properties also have $C_{1-5}$ alkyl moieties selected from the group consisting of methyl, ethyl, propyl and n-propyl. In the most preferred embodiment, the ester is a fatty acid methyl ester.

The polyunsaturated vegetable oils suitable for preparing the fatty acid $C_{1-5}$ ester can include genetically modified oil, soybean oil, linseed oil, corn oil, sunflower oil, canola oil, rapeseed oil, coconut oil, palm kernel oil, palm oil, cottonseed oil, peanut oil, olive oil, tall oil, safflower oil and derivatives thereof. Preferably, the vegetable oil is a polyunsaturated oil selected from the group above. Most preferably, the polyunsaturated vegetable oil is low in C18:3 or higher fatty acids. Although any polyunsaturated oil that has sufficiently low levels of C18:3 or higher fatty acids is suitable for the present method, preferably, the vegetable oil is safflower oil, sunflower oil or corn oil. Preferred oils contain less than about 2 percent of C18:3 or higher polyunsaturated fatty acids. More preferably, the oils contain less than about 1 percent of C18:3 or higher polyunsaturated fatty acids. Also preferred are polyunsaturated vegetable oils containing less than about 2 percent linolenic acid. More preferably, the linolenic content is less than about 1 percent.

Regarding the amount of borohydride that is sufficient to perform this embodiment, by routine experimentation, a skilled artisan will quickly be able to determine the amount of borohydride necessary for a given reaction.

Preferably, the borohydride is selected from the group consisting of sodium borohydride, potassium borohydride and lithium borohydride. Preferably, the borohydride is present in an amount between about 1.0 percent and 0.0001 percent by weight of the reactants and catalyst. More preferably, the amount of borohydride is between about 0.1 percent to about 0.001 percent. It has been found that sodium borohydride present in an amount between about 0.01 percent to about 0.001 percent by weight of the reactants and catalyst yields a glycol monoester mixture that possesses the desirable light color.

The polyol is selected from dihydroxy polyols, which include ethylene glycol, propylene glycol, diethylene glycol, dipropylene glycol and the like. The preferred polyol is propylene glycol, which includes individual isomers and d,l-propylene glycol.

The catalyst selected for use in this embodiment can be any catalyst generally known in the art for use in transesterification and esterification reactions. Preferably, the catalyst used in the present process is an alkaline catalyst. More preferably, the catalyst is selected from the group consisting of sodium methoxide, sodium ethoxide, potassium methoxide and potassium ethoxide. Most preferably, the catalyst used in the present process is sodium methoxide.

In this embodiment, the monoester mixture produced by the present method preferably has a peroxide value below about 50. More preferably, the peroxide value is below about 25. Most preferably, the peroxide value is below about 10.

A process has been developed using borohydride to inhibit development of color in the preparation of glycol fatty acid monoesters from fatty acid $C_{1-5}$ alkyl esters. The present process is more economical because it can be performed without a molecular distillation or other decoloration steps. The present process utilizes borohydride to produce a polyol ester mixture that is lighter in color than a polyol ester mixture synthesized by the same method without using sodium borohydride. Such light-colored ester products are, among other uses, suitable for use in compositions where a monoester mixture is appropriate and any discoloration due to the monoester mixture is undesirable. Further, the monoester mixture was similar in color to current commercially available coalescing aids such as TMB.

EXAMPLES

Example 1

Preparation of Propylene Glycol Fatty Acid Esters without Addition of Sodium Borohydride Methyl esters of sunflower oil fatty acids (sunflower methyl esters) from Columbus Foods Company (Chicago, Ill.) were distilled at the Stepan Company (Elwood, Ill.) to yield a water-clear, colorless distilled sunflower methyl ester product. Distilled sunflower methyl esters had a peroxide value (PV) of 3.0 and contained essentially no moisture. A 1000 ml 3-neck round-bottom flask was fitted with a stirrer, heating mantle, reflux condenser, nitrogen sparge, and vacuum off the condenser. To this flask was charged 200 g of the above distilled sunflower methyl esters, 250 g anhydrous propylene glycol (Aldrich Chemical Co.), and 0.55 g sodium methoxide catalyst.

Begin heating the combined starting materials with good agitation to 60° C. under house vacuum (about 25 inches Hg vacuum) with a slight nitrogen sparge. Continue heating in this manner to 85° C. over a 4.5 hour period. Methanol by-product was lost to the house vacuum while propylene glycol vapors condensed on the reflux condenser. After the 4.5 hours, the contents of the reactor were cooled to about 60° C. Vacuum was discontinued, and the catalyst was neutralized with 1.25 g citric acid in 20 ml of deionized (DI) water. The reactor was stirred for about 20 minutes. Stirring was stopped and the contents of the reactor were allowed to settle. The contents separated into 2 layers. The top layer was collected and allowed to cool in a separatory funnel. About 200 ml of hexane was added and mixed. The product solution was washed 4 times in the separatory funnel with equal amounts of DI water. After 4 wash steps, the top layer was collected in a large beaker with stirrer and was dried of moisture by the addition of anhydrous magnesium sulfate. After stirring for 30 minutes, the solid magnesium sulfate was filtered from the solution and the hexane was remove by rotary evaporation. Final residual hexane and propylene glycol were removed on a lab wiped film evaporator.

Final product was composed of predominately propylene glycol fatty acid monoesters, some propylene glycol fatty acid diesters, and a small amount of residual methyl esters and residual compounds. Lovibond color of the product was 0.9 Red and 4.3 Yellow.

Example 2

Preparation of Propylene Glycol Fatty Acid Esters with Addition of Sodium Borohydride Propylene glycol fatty acid esters were prepared from the same starting materials and by the same procedure as in Example 1, except that 0.1 g of fresh sodium borohydride was charged with the sodium methoxide catalyst into the reactor. After the reaction, neutralization, washing, drying, and stripping of residual volatiles on the lab evaporator, the propylene glycol fatty acid ester product was similar to that of Example 1, except that Example 2 had a Lovibond color of 0.0 Red and 0.3 Yellow and appeared water clear and colorless to the eye.

Example 3

Pilot Scale Preparation of Propylene Glycol Fatty Acid Esters with Addition of Sodium Borohydride Methyl esters of sunflower oil fatty acids (sunflower methyl esters) were prepared from traditional sunflower oil at Columbus Foods Company (Chicago, Ill.). These sunflower methyl esters were received at the Stepan Company (Elwood, Ill.) from Columbus Foods and were distilled in an 800 gallon reactor to yield a water-clear, colorless distilled sunflower methyl ester product. Distilled sunflower methyl esters had a peroxide value (PV) of about 3.0 and contained 0.009% water. A 200 gallon pilot reactor was charged with 720 pounds of propylene glycol (280 ppm water) and 482 pounds of the distilled sunflower methyl esters at 28° C. Agitation was set at 110 rpm. A sample of the reactor contents tested as 310 ppm moisture and an acid value (AV) of 0.07. Contents were held under nitrogen. Three times nitrogen was added to the reactor headspace and three times the reactor headspace was evacuated under vacuum to remove oxygen. Reactor was then held under vacuum (pressure of 2.1 psia). While under vacuum, 6.5 pounds of 21% sodium methylate in methanol and 204 grams of sodium borohydride in 10 pounds of propylene glycol were added. Another 10 pounds of propylene glycol was added to flush any residual catalyst or borohydride. Slight nitrogen sparge was introduced while maintaining vacuum (reactor pressure now 2.5 psia). Controllers began to heat the reactor to 110° C. After about 30 minutes of heating, the temperature was about 82° C. and the pressure was 3.5 psia. The first condensate (methanol) collected on the sight glass. After about 40 minutes at 84° C., foaming began as methanol evolved in earnest. Heating continued and good "boil-up" of methanol continued. Methanol vapor left the reactor and was condensed by a glycol chiller condenser and collected in a condenser reservoir. After 3 hours 20 minutes, the reactor reached 110° C. and 2.9 psia. Reactor was heated further while maintaining about 2.9 psia. After about 4 hours, temperature was about 113° C. and pressure was 2.9 psia. At about 6 hours, agitation was increased to 124 rpm. Temperature was continually increased and measured. After 8 hours, temperature was at 138° C. and a sample of the product was taken and analyzed. Residual methyl esters were 2% of all the fatty acid containing compounds. Heating continued until the reaction was at about 138° C. and 2.5 psia pressure. After 11 hours, temperature was at 138° C. and another sample of the product was taken and analyzed. Residual methyl esters were 1%. After 13 hours 20 minutes, the reactor started to be cooled. After 14 hours 30 minutes the reactor was at 52° C. The catalyst was neutralized by addition of 4.3 pounds of citric acid in 6 pounds of water. After 15 minutes of mixing the reactor was sampled and checked for pH (pH was 5.4).

The reactor was heated once again (slowly ramping up) under vacuum to strip off moisture and residual unreacted propylene glycol. After about 6 hours with temperatures up to 140° C. and pressure of about 1.0 psia, a sample was taken (0.9% residual propylene glycol). Reactor was cooled to about 50° C. About 900 pounds of soft water was added and mixed with the product for about 30 minutes. Agitation was stopped and after settling, the water layer was drained away. The washed sample contained 0.02% propylene glycol. Moisture was then removed to less that 0.072% water.

The final product was analyzed to contain 88.8% propylene glycol fatty acid monoesters, 10.5% propylene glycol fatty acid diesters, 0.4% other mixed glycol monoesters, 0.07% propylene glycol, and 0.06% fatty acid methyl esters. Lovibond color on the PGME final product was 0.2 Red, 0.5 Yellow.

Having now fully described this invention, it will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A process of producing a polyol monoester mixture comprising,
   a. combining a fatty acid $C_{1-5}$ alkyl ester, wherein said $C_{1-5}$ alkyl ester is derived from a polyunsaturated vegetable oil containing less than about 2 percent of C18:3 or higher polyunsaturated fatty acids, said polyunsaturated vegetable oil selected from the group consisting of genetically modified oil, soybean oil, linseed oil, corn oil, sunflower oil, canola oil, rapeseed oil, coconut oil, palm kernel oil, palm oil, cottonseed oil, peanut oil, olive oil, tall oil, safflower oil and derivatives and mixtures thereof, with a polyol in the presence of a catalyst and borohydride, and
   b. heating said combined fatty acid $C_{1-5}$ alkyl ester and polyol in the presence of said catalyst and borohydride, wherein a polyol monoester mixture that is light in color is produced.

2. The process of claim 1 further comprising, distilling said fatty acid $C_{1-5}$ alkyl ester to prepare a distilled fatty acid $C_{1-5}$ alkyl ester prior to combining with said polyol.

3. The process of claim 2, wherein a molecular distillation is not performed to produce said monoester mixture.

4. The process of claim 2, wherein a decoloration step selected from the group consisting of carbon treatment and bleaching is not performed to produce said monoester mixture.

5. The process of claim 1, wherein said catalyst is selected from the group consisting of sodium methoxide, sodium ethoxide, potassium methoxide and potassium ethoxide.

6. The process of claim 5, wherein said catalyst is sodium methoxide.

7. The process of claim 1 wherein said heating is between about 70° C. and about 160° C.

8. The process of claim 7, wherein said heating is between about 100° C. and about 140° C.

9. The process of claim 1, wherein said vegetable oil is safflower oil, sunflower oil or corn oil.

10. The process of claim 1, wherein said polyunsaturated vegetable oil contains less than about 2 percent linolenic acid.

11. The process of claim 10, wherein said polyunsaturated vegetable oil contains less than about 1 percent linolenic acid.

12. The process of claim 1, wherein said monoester mixture is a composition comprising at least about 80 percent polyol monoester.

13. The process of claim 1, wherein said monoester mixture has a Lovibond color below about 0.6 Red and below about 1.5 Yellow.

14. The process of claim 13, wherein said monoester mixture has a Lovibond color below about 0.4 Red and below about 1.0 Yellow.

15. The process of claim 1, wherein said borohydride is present in an amount between about 1.0 percent to about 0.0001 percent by weight relative to the weight of reactants and catalyst.

16. The process of claim 1, wherein said borohydride is selected from the group consisting of sodium borohydride, potassium borohydride and lithium borohydride.

17. The process of claim 1, wherein said polyol is selected from the group consisting of ethylene glycol, propylene glycol, diethylene glycol and dipropylene glycol.

18. The process of claim 17, wherein said polyol is propylene glycol.

19. The process of claim 1, wherein said fatty acid $C_{1-5}$ alkyl ester is a fatty acid methyl ester.

20. The process of claim 1, wherein said polyol monoester mixture has a peroxide value below about 50.

21. The process of claim 20, wherein said polyol monoester mixture has a peroxide value below about 10.

22. A process of producing a monoester mixture comprising,
(a) distilling a fatty acid $C_{1-5}$ alkyl ester containing less than about 2 percent C18:3 or higher polyunsaturated fatty acids to produce a distilled fatty acid $C_{1-5}$ alkyl ester,
(b) combining said distilled fatty acid $C_{1-5}$ alkyl ester with a polyol to produce a first mixture,
(c) introducing a catalyst and borohydride to said first mixture,
(d) heating said first mixture to a temperature between about 70° C. and about 160° C. to produce a second mixture,
(e) cooling and neutralizing said second mixture with an acid, and
(f) separating a monoester mixture from said second mixture, wherein a monoester mixture is produced.

23. The process of claim 22, wherein a molecular distillation is not performed to produce said monoester mixture.

24. The process of claim 22, wherein a decoloration step selected from the group consisting of carbon treatment and bleaching is not performed to produce said monoester mixture.

25. The process of claim 22, wherein said catalyst is selected from the group consisting of sodium methoxide, sodium ethoxide, potassium methoxide and potassium ethoxide.

26. The process of claim 25, wherein said catalyst is sodium methoxide.

27. The process of claim 22, wherein said fatty acid $C_{1-5}$ alkyl ester is derived from a vegetable oil selected from the group consisting of genetically modified oil, soybean oil, linseed oil, corn oil, sunflower oil, canola oil, rapeseed oil, coconut oil, palm kernel oil, palm oil, cottonseed oil, peanut oil, olive oil, tall oil, safflower oil and derivatives and mixtures thereof.

28. The process of claim 27, wherein said vegetable oil is safflower oil, sunflower oil or corn oil.

29. The process of claim 27, wherein said vegetable oil is a polyunsaturated vegetable oil that contains less than about 2 percent of C18:3 or higher polyunsaturated fatty acids.

30. The process of claim 29, wherein said polyunsaturated vegetable oil contains less than about 2 percent of linolenic acid.

31. The process of claim 29, wherein said polyunsaturated vegetable oil contains less than about 1 percent of linolenic acid.

32. The process of claim 22, wherein said monoester mixture is a composition comprising at least about 80 percent polyol monoester.

33. The process of claim 22, wherein said monoester mixture has a Lovibond color lower than about 0.6 Red and below about 1.5 Yellow.

34. The process of claim 33, wherein said monoester mixture has a Lovibond color lower than about 0.4 Red and below about 1.0 Yellow.

35. The process of claim 22, wherein said borohydride is selected from the group consisting of sodium borohydride, potassium borohydride and lithium borohydride.

36. The process of claim 35, wherein said borohydride is sodium borohydride.

37. The process of claim 35, wherein said borohydride is present in an amount between about 1.0 percent to about 0.0001 percent by weight relative to the weight of reactants and catalyst.

38. The process of claim 22, wherein said monoester mixture has a peroxide value below about 50.

39. The process of claim 38, wherein said monoester mixture has a peroxide value below about 10.

40. A process of producing a monoester mixture comprising, combining a distilled fatty acid $C_{1-5}$ alkyl ester of a polyunsaturated vegetable oil containing less than about 2 percent C18:3 or higher polyunsaturated fatty acids with propylene glycol in the presence of a catalyst and borohydride to produce a monoester mixture having a Lovibond color below about 0.6 Red and below about 1.5 Yellow.

41. The process of claim 40, provided that a molecular distillation, carbon decoloration or bleaching step is not performed to produce said monoester mixture.

42. The process of claim 41, wherein said catalyst is selected from the group consisting of sodium methoxide, sodium ethoxide, potassium methoxide and potassium ethoxide.

43. The process of claim 42, wherein said borohydride is selected from the group consisting of sodium borohydride, potassium borohydride and lithium borohydride.

44. The process of claim 43, wherein said borohydride is sodium borohydride.

45. The process of claim 44, wherein said sodium borohydride is present in an amount between about 1.0 percent to about 0.0001 percent by weight relative to the weight of reactants and catalyst.

46. The process of claim 45, wherein said monoester mixture has a peroxide value below about 50.

47. The process of claim 45, wherein said monoester mixture has a peroxide value below about 25.

48. The process of claim 47, wherein said monoester mixture contains at least about 80 percent propylene glycol monoester.

49. The process of claim 48, wherein said fatty acid $C_{1-5}$ alkyl ester is a fatty acid methyl ester.

50. The process of claim 49, wherein said polyunsaturated vegetable oil is safflower oil, sunflower oil or corn oil.

51. The process of claim 50, wherein said Lovibond color is below about 0.4 Red and below about 1.0 Yellow.

52. A process of producing a polyol monoester mixture comprising:
   a. combining a distilled fatty acid $C_{1-5}$ alkyl ester, wherein said $C_{1-5}$ alkyl ester is derived from a vegetable oil selected from the group consisting of genetically modified oil, soybean oil, linseed oil, corn oil, sunflower oil, canola oil, rapeseed oil, coconut oil, palm kernel oil, palm oil, cottonseed oil, peanut oil, olive oil, tall oil, safflower oil and derivatives and mixtures thereof, with a polyol in the presence of a catalyst and borohydride, and
   b. heating said combined fatty acid $C_{1-5}$ alkyl ester and polyol in the presence of said catalyst and borohydride, thereby producing a polyol monoester mixture having a Lovibond color below about 0.6 Red and below about 1.5 Yellow;
   wherein a decoloration step selected from the group consisting of carbon treatment and bleaching is not performed to produce said monoester mixture.

53. The process of claim 52, wherein said monoester mixture has a Lovibond color below about 0.4 Red and below about 1.0 Yellow.

54. The process of claim 52, wherein said borohydride is present in an amount between about 1.0 percent to about 0.0001 percent by weight relative to the weight of reactants and catalyst.

55. The process of claim 52, wherein said borohydride is selected from the group consisting of sodium borohydride, potassium borohydride and lithium borohydride.

56. The process of claim 52, wherein said catalyst is selected from the group consisting of sodium methoxide, sodium ethoxide, potassium methoxide and potassium ethoxide.

57. The process of claim 52, wherein said polyol is selected from the group consisting of ethylene glycol, propylene glycol, diethylene glycol and dipropylene glycol.

* * * * *